(12) United States Patent
Gramza et al.

(10) Patent No.: US 7,976,487 B2
(45) Date of Patent: Jul. 12, 2011

(54) FASTENER TABS AND STRAPPING SYSTEM FOR ORTHOPEDIC SUPPORTS AND METHOD OF USING SAME

(75) Inventors: Beth Gramza, Cincinnati, OH (US); Scott D. McCormick, Cincinnati, OH (US); Edward L. Weaver, II, Milford, OH (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 11/609,115

(22) Filed: Dec. 11, 2006

(65) Prior Publication Data

US 2007/0167892 A1  Jul. 19, 2007

Related U.S. Application Data

(60) Provisional application No. 60/749,944, filed on Dec. 13, 2005.

(51) Int. Cl.
*A61F 5/00* (2006.01)

(52) U.S. Cl. .............................. 602/20; 602/21; 602/23

(58) Field of Classification Search .............. 602/20–22, 602/60–64; 128/878–880, 882
See application file for complete search history.

(56) References Cited

U.S. PATENT DOCUMENTS

| | | | |
|---|---|---|---|
| 2,002,527 A | 5/1935 | Dorogi et al. | |
| 3,408,438 A | 10/1968 | Staunton | |
| 3,926,186 A | 12/1975 | Nirschl | |
| 4,021,866 A * | 5/1977 | Wasko | 623/57 |
| 4,047,250 A * | 9/1977 | Norman | 2/161.1 |
| 4,212,746 A | 7/1980 | Tholema et al. | |
| 4,491,556 A | 1/1985 | Fujii et al. | |
| 4,573,455 A | 3/1986 | Hoy | |
| 4,603,690 A | 8/1986 | Skeen | |
| 4,626,185 A | 12/1986 | Monnet | |
| 4,726,362 A | 2/1988 | Nelson | |
| 4,844,057 A | 7/1989 | Hoy | |
| 4,844,094 A | 7/1989 | Grim | |
| 4,938,207 A | 7/1990 | Vargo | |
| 5,025,782 A | 6/1991 | Salerno | |
| 5,085,917 A | 2/1992 | Hodnett, III | |
| 5,139,477 A | 8/1992 | Peters | |
| 5,171,508 A | 12/1992 | Ishizu et al. | |

(Continued)

FOREIGN PATENT DOCUMENTS

FR  2 600 933  1/1988

*Primary Examiner* — Michael A. Brown
(74) *Attorney, Agent, or Firm* — Lisa P. Fulton; Elizabeth A. Gallo

(57) ABSTRACT

An orthopedic support for supporting a joint of a wearer is provided and includes a sheet of flexible material having a proximal edge and a distal edge configured to extend at least partially around a portion of a wearer's anatomy and a pair of opposing lateral edges configured to at least partially enclose the portion of the wearer's anatomy. The support also includes at least one strap attached to the sheet of material and configured to extend over one of the lateral edges. In addition, the support includes at least one fastener tab secured to a free end of a respective strap, wherein the fastener tab supports fastening material that is configured to attach to at least one of the strap and sheet of material to secure the sheet of material about the portion of the wearer's anatomy.

23 Claims, 16 Drawing Sheets

U.S. PATENT DOCUMENTS

| | | | |
|---|---|---|---|
| 5,288,287 A | 2/1994 | Castillo et al. | |
| 5,326,523 A | 7/1994 | Gustavel et al. | |
| 5,385,538 A | 1/1995 | Mann | |
| 5,445,602 A | 8/1995 | Grim et al. | |
| 5,454,706 A | 10/1995 | Midorikawa et al. | |
| 5,462,517 A | 10/1995 | Mann | |
| 5,552,472 A | 9/1996 | Kerr et al. | |
| 5,626,557 A | 5/1997 | Mann | |
| 5,693,007 A | 12/1997 | Townsend | |
| 5,714,175 A | 2/1998 | Masui et al. | |
| 5,759,464 A | 6/1998 | Matsumoto et al. | |
| 5,823,981 A | 10/1998 | Grim et al. | |
| 5,997,793 A | 12/1999 | Lahnala | |
| 6,024,712 A | 2/2000 | Iglesias et al. | |
| 6,059,743 A | 5/2000 | Reinhardt et al. | |
| 6,190,344 B1 * | 2/2001 | Bobroff | 602/21 |
| 6,214,261 B1 | 4/2001 | Smarto et al. | |
| 6,228,290 B1 | 5/2001 | Reames et al. | |
| 6,258,409 B1 | 7/2001 | Sale et al. | |
| 6,348,170 B1 | 2/2002 | Masui et al. | |
| 6,375,699 B1 | 4/2002 | Beck | |
| 6,398,903 B1 | 6/2002 | Stedron et al. | |
| 6,413,461 B1 | 7/2002 | Kobayashi et al. | |
| 6,471,276 B1 | 10/2002 | Brunsman et al. | |
| 6,479,006 B1 | 11/2002 | Kaufmann | |
| 6,482,167 B2 | 11/2002 | Grim et al. | |
| 6,558,590 B1 | 5/2003 | Stewart | |
| 6,589,272 B1 * | 7/2003 | Sheikh | 607/108 |
| 6,630,043 B2 | 10/2003 | Sloot | |
| 6,743,188 B1 | 6/2004 | Littmann et al. | |
| 6,743,322 B2 | 6/2004 | Sloot | |
| 6,893,410 B1 | 5/2005 | Hely | |
| 7,004,919 B2 | 2/2006 | Gaylord et al. | |
| 7,037,285 B2 * | 5/2006 | Yewer, Jr. | 602/21 |
| 7,237,270 B2 | 7/2007 | Crye et al. | |
| 2002/0163101 A1 | 11/2002 | Cotton et al. | |
| 2003/0176826 A1 | 9/2003 | Scott | |
| 2003/0204156 A1 | 10/2003 | Nelson et al. | |
| 2004/0031534 A1 | 2/2004 | Schwartz | |

* cited by examiner

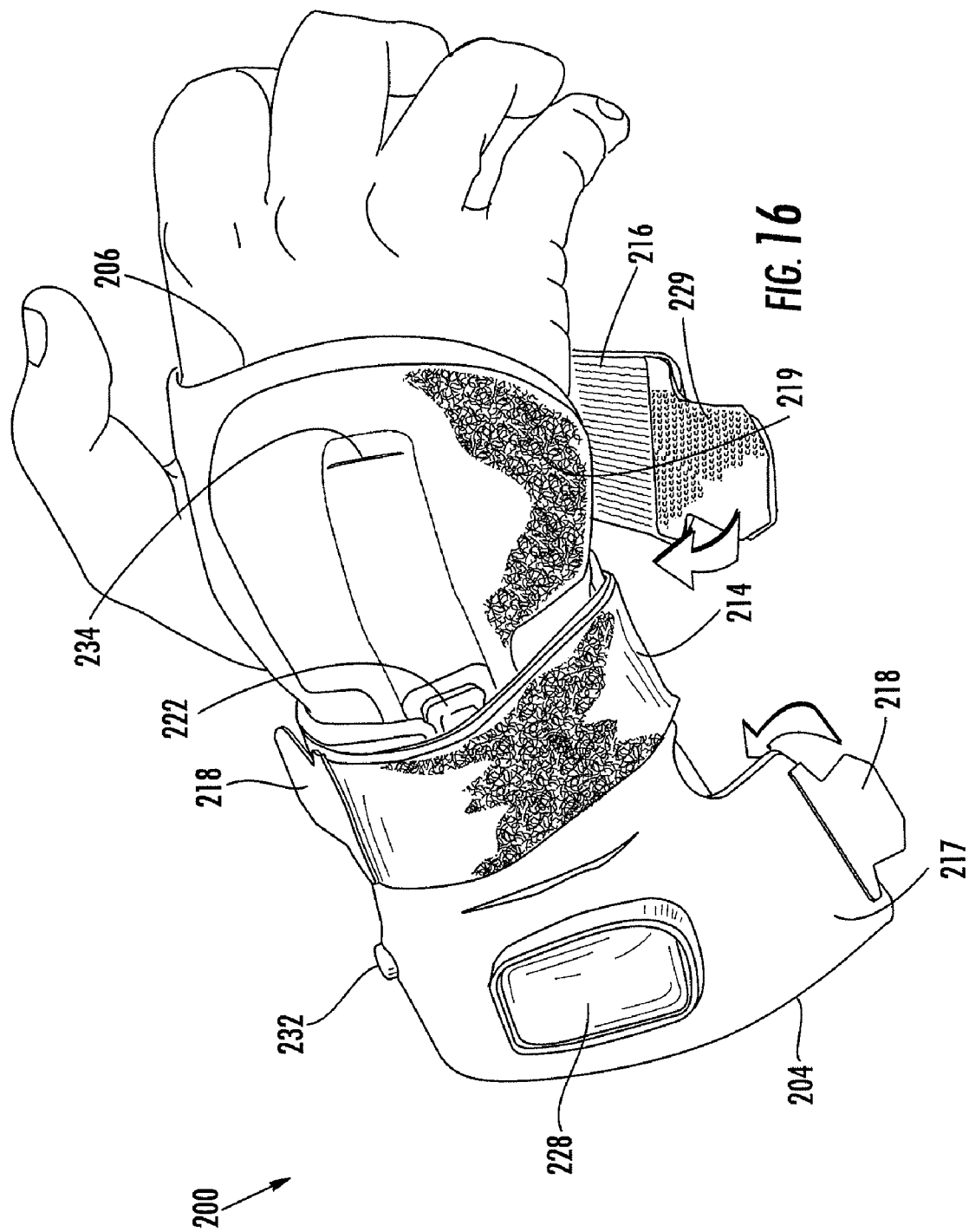

FASTENER TABS AND STRAPPING SYSTEM FOR ORTHOPEDIC SUPPORTS AND METHOD OF USING SAME

CROSS REFERENCE TO RELATED APPLICATIONS

The present application claims priority from U.S. Provisional Application No. 60/749,944 entitled FASTENER TABS AND STRAPPING SYSTEM FOR ORTHOPEDIC SUPPORTS AND METHOD OF USING SAME filed Dec. 13, 2005, the contents of which are incorporated herein by reference.

BACKGROUND OF THE INVENTION

1. Field of the Invention

Embodiments of the present invention relate to the field of orthopedic supports, and more particularly, to orthopedic supports having one or more fastener tabs and/or a strapping system for securing the support to a limb of the wearer.

2. Description of Related Art

Orthopedic supports commonly use hook-and-loop fasteners for securing the support on a wearer's limb. The fasteners are typically a one-piece design that includes hook material on one surface and a non-hook bearing surface on the opposite surface. The fasteners are typically attached, such as by stitching, to a free end of a strap and used to secure the strap about the wearer's limb. The fasteners are typically pliable but lack durability, and the outer surface of the fastener may be irritable to the wearer's skin or clothing.

Various techniques have been developed to secure an orthopedic support to a wearer's limb. Namely, a plurality of straps are typically attached to a sheet of material and employed to secure the sheet of material to the wearer's limb. For example, U.S. Pat. No. 6,893,410 to Hely discloses a multi-adjustable wrist brace that includes a pair of flaps that are secured to the wearer's wrist with tightening strands attached to a tightener flap. As the tightener flap of Hely is tensioned, the strands are also tensioned. The wrist brace of Hely also includes an auxiliary strap that extends between the wearer's thumb and index finger that includes connective material that may attach to the material on the flaps. Both the tightener flap and auxiliary strap may include hook material that is complementary with pile material on the flaps of the wrist brace. In addition, the wrist brace of Hely may include a web that interconnects the two flaps to hold the flaps apart and enable a wearer to insert his or her wrist therein.

Despite these improvements in providing stability for a joint while allowing for some degree of mobility, additional innovations in orthopedic supports to promote better comfort and/or support for the wearer are also desired. In particular, although techniques have been developed to secure orthopedic supports to a wearer's limb, there is a need for fasteners and a strapping system that more effectively secure the support to the wearer's limb and are more economical and efficient to manufacture. Furthermore, techniques are needed to more easily position, secure, and readjust an orthopedic support on a wearer's limb.

It would therefore be advantageous to provide an orthopedic support that may be effectively secured on the wearer without sacrificing mobility. In addition, it would be advantageous to provide an orthopedic support that includes a strapping system that may be easily manufactured and used for various orthopedic applications.

BRIEF SUMMARY OF THE INVENTION

Embodiments of the present invention address the above needs and achieve other advantages by providing an orthopedic support for supporting a portion of a limb of the wearer. The orthopedic support generally includes a sheet of flexible material for conforming to a portion of the wearer's anatomy, as well as straps for securing the sheet of material on the wearer.

In one embodiment, a wrist support of the present invention includes a sheet of material including at least one strap for securing the sheet of material about a wearer's wrist. The wrist support includes at least one fastener tab that is attached to a free end of a respective strap. The fastener tab includes fastening material on one surface, where the fastening material on the fastener tab is complementary to fastening material on the sheet of material or a respective strap.

The sheet of material, according to one variation of the present invention, includes opposing lateral edges and opposing proximal and distal edges. The sheet of material is configured to wrap about a wearer's wrist between the hand and forearm, and may include a thumb opening for accommodating a wearer's thumb. The sheet of material could be a laminate or non-laminate material.

The wrist support includes a plurality of straps extending from respective lateral edges of the sheet of material. Typically, at least one strap extends from a first lateral edge proximate to the proximal edge, and at least one additional strap extends from a second lateral edge and proximate to the distal edge. A third strap may extend from the first or second lateral edge approximately midway between the proximal and distal edges. Each of the straps includes fastening material and associated fastener tabs on a free end that attaches to complementary fastening material on the sheet of material or a respective strap.

At least one strap guide may be secured to an outer surface of the sheet of material. The strap guide is capable of slidably receiving a strap therein and guiding the strap along the sheet of material. Furthermore, at least one pass may be secured about its outer perimeter to the sheet of material. The pass is configured to slidably receive a strap therein and guide the strap through the sheet of material. Moreover, at least one strap ring may be secured to a lateral edge of the sheet of material and be configured to slidably receive a strap therein. The strap extending through the strap ring is capable of looping back over itself to tension the strap, as well as attach to itself. The strap could be a longitudinal strap that substantially encircles the wearer's wrist. The strap guide, pass, and ring may be a polymeric material, such as polyethylene, and could be injection molded directly to the sheet of material.

The wrist support may also include an inflatable bladder. The inflatable bladder typically includes a pump operable to inflate the bladder to a desired pressure, as well as a release valve for selectively releasing pressure from the bladder. The bladder may include a palmar bladder that lies within the palm of the wearer. Furthermore, the palmar bladder may be configured to extend adjacent to at least one palmar stay. The palmar stay may be longitudinal and configured to extend from the forearm to the palm of the wearer. The wrist support may also include a dorsal stay positioned adjacent to a dorsal portion of the wearer's hand. In one variation, the wrist support includes pockets defined in the sheet of material for accommodating each of the palmar and dorsal stays, as well as respective openings defined in each pocket for removably inserting respective stays therein.

The support may also include fastener tabs that are attached to respective straps and are utilized to support respective fastening material. Each fastener tab is typically a polymeric material, such as polyethylene. The fastener tab could be formed by injection-molding. The fastening material may be integrally formed with a respective fastener tab or separately attached thereto. Each fastener tab may also include at least one prong that is capable of engaging an opening in the free end of a respective strap. Moreover, at least a portion of the fastener tab and fastening material may flare outwardly, such that a portion of the fastener tab and fastening material may extend over a respective free end of the strap and engage opposed surfaces of the free end.

Embodiments of the present invention may provide many advantages. For instance, the fastener tabs may provide increased support and durability to the fastening material attached to its opposite surface without increasing the incidence of irritation to the wearer's skin or clothing. The fastener tabs are typically a polymeric material that may be easily fabricated and assembled to the fastening material and/or sheet of material. In addition, the strapping configuration of the orthopedic support provides a "ready-to-use" configuration that enables a wearer to initially position the support on the wearer's limb and further secure the support thereon. The strapping system provides components (e.g., the strap guide, pass, and ring) that may be easily manufactured and assembled to the sheet of material. Furthermore, the fastener tabs and strapping system are also capable of being used with a variety of orthopedic supports, including the knee, ankle, and wrist.

BRIEF DESCRIPTION OF THE SEVERAL VIEWS OF THE DRAWING(S)

Having thus described the invention in general terms, reference will now be made to the accompanying drawings, which are not necessarily drawn to scale, and wherein:

FIG. 12A is a cross-sectional view of a fastener tab secured to a free end of a strap according to one embodiment of the present invention; and FIGS. 13-16 are perspective views of a sequence of securing the wrist support to a wearer's wrist according to one embodiment of the present invention.

DETAILED DESCRIPTION OF THE INVENTION

The present invention now will be described more fully hereinafter with reference to the accompanying drawings, in which some, but not all embodiments of the invention are shown. Indeed, the invention may be embodied in many different forms and should not be construed as limited to the embodiments set forth herein; rather, these embodiments are provided so that this disclosure will satisfy applicable legal requirements. Like numbers refer to like elements throughout.

Generally, embodiments of the present invention provide an orthopedic support that includes a sheet of flexible material for wrapping about and conforming to a portion of a wearer's anatomy. One or more straps are configured for securing the sheet of material about the wearer's anatomy. In addition, the orthopedic support includes fastener tabs, typically polymeric material, that may be secured to fastening material and attached to free ends of a respective strap. The fastener tabs may be used in conjunction with a strapping system for securing the orthopedic support on a wearer's limb. The orthopedic support could be worn on a limb or portions of a limb of a wearer, such as, for example, on a wrist, knee, ankle, elbow, back, arm, forearm, leg, or thigh.

Knee Support

Figure 1:
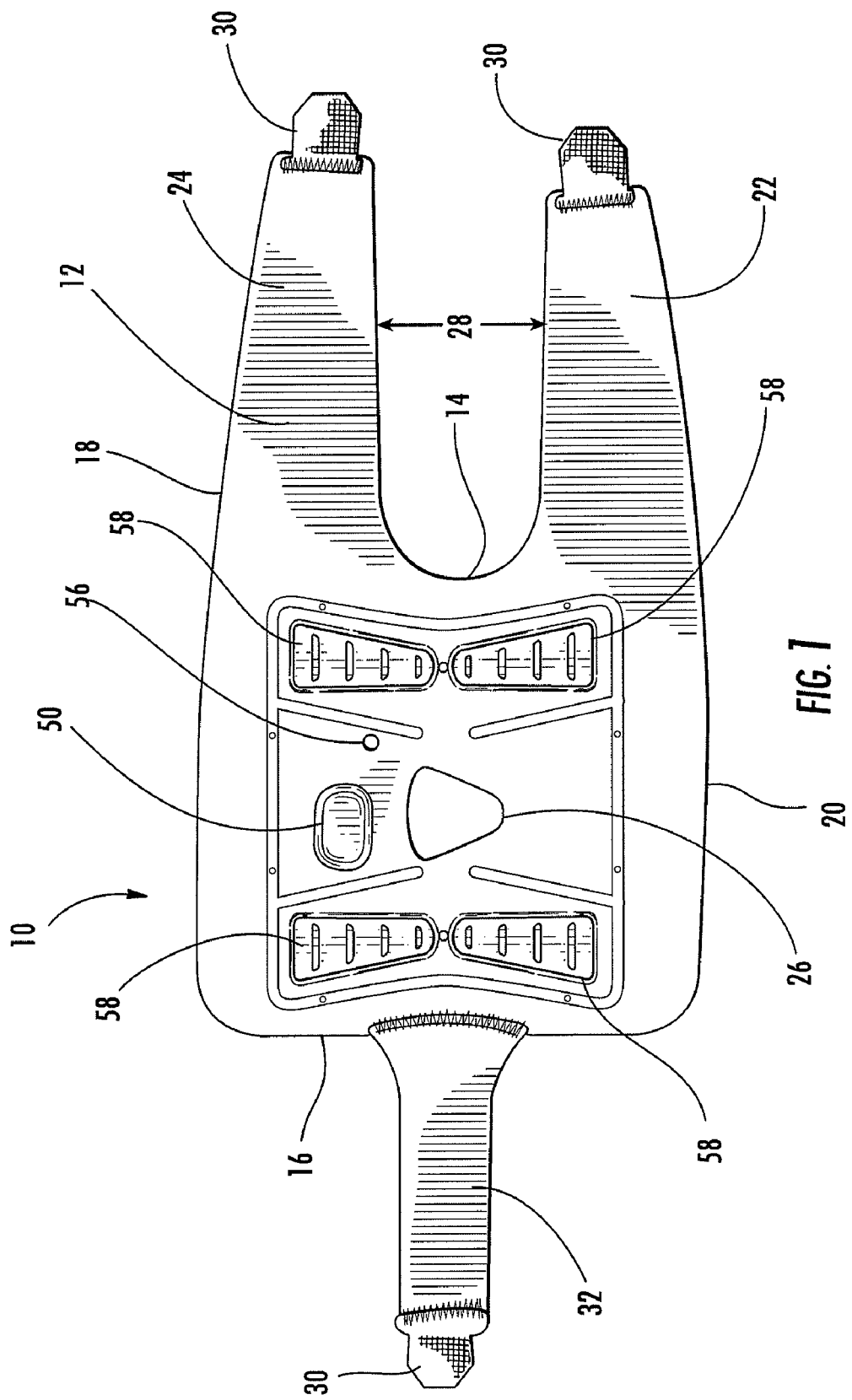
FIG. 1 is a plan view of an outer surface of a knee support according to one embodiment of the present invention.
Figure 2:
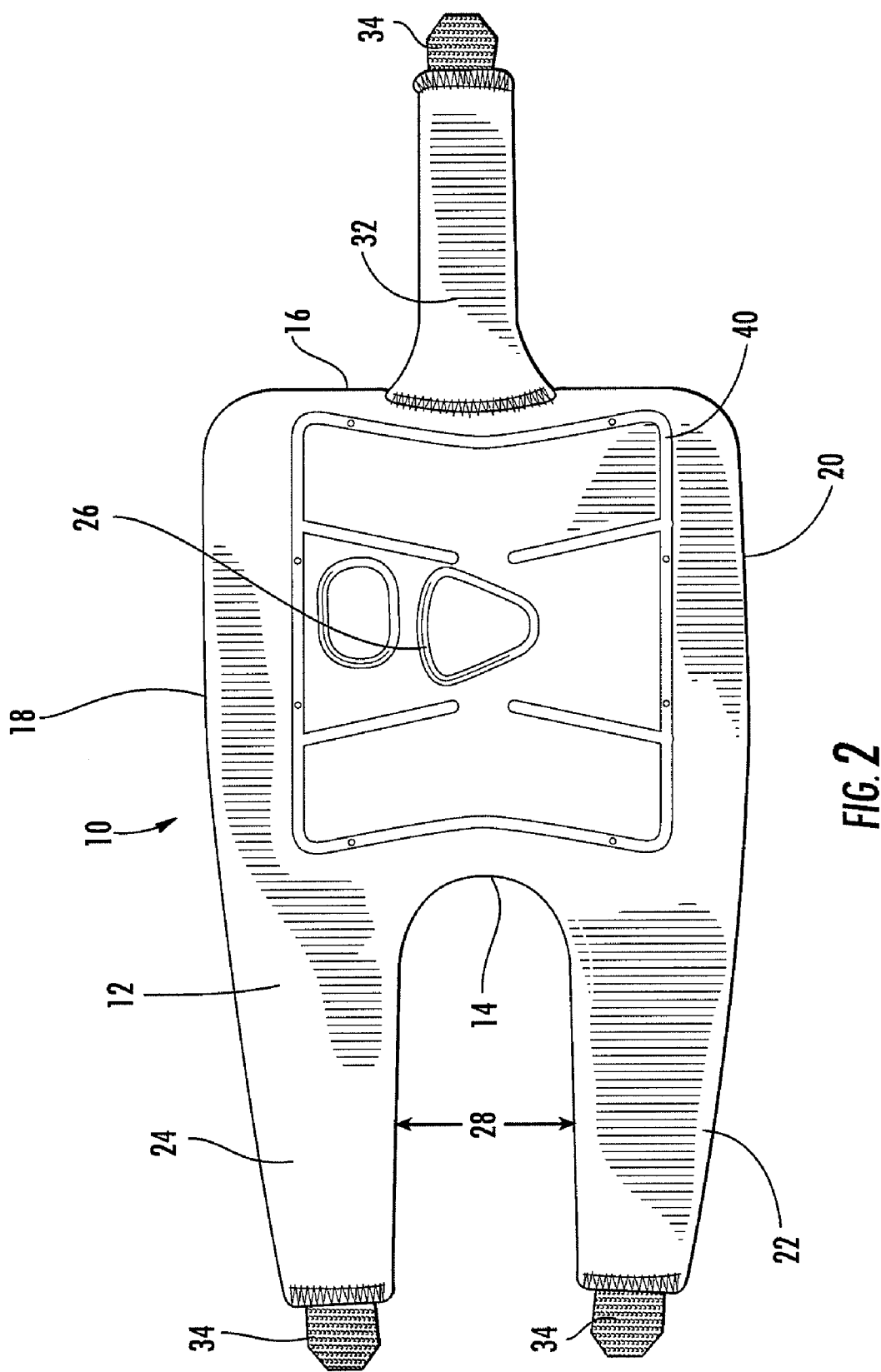
FIG. 2 is a plan view of an inner surface of the knee support shown in FIG. 1.
Figure 3:
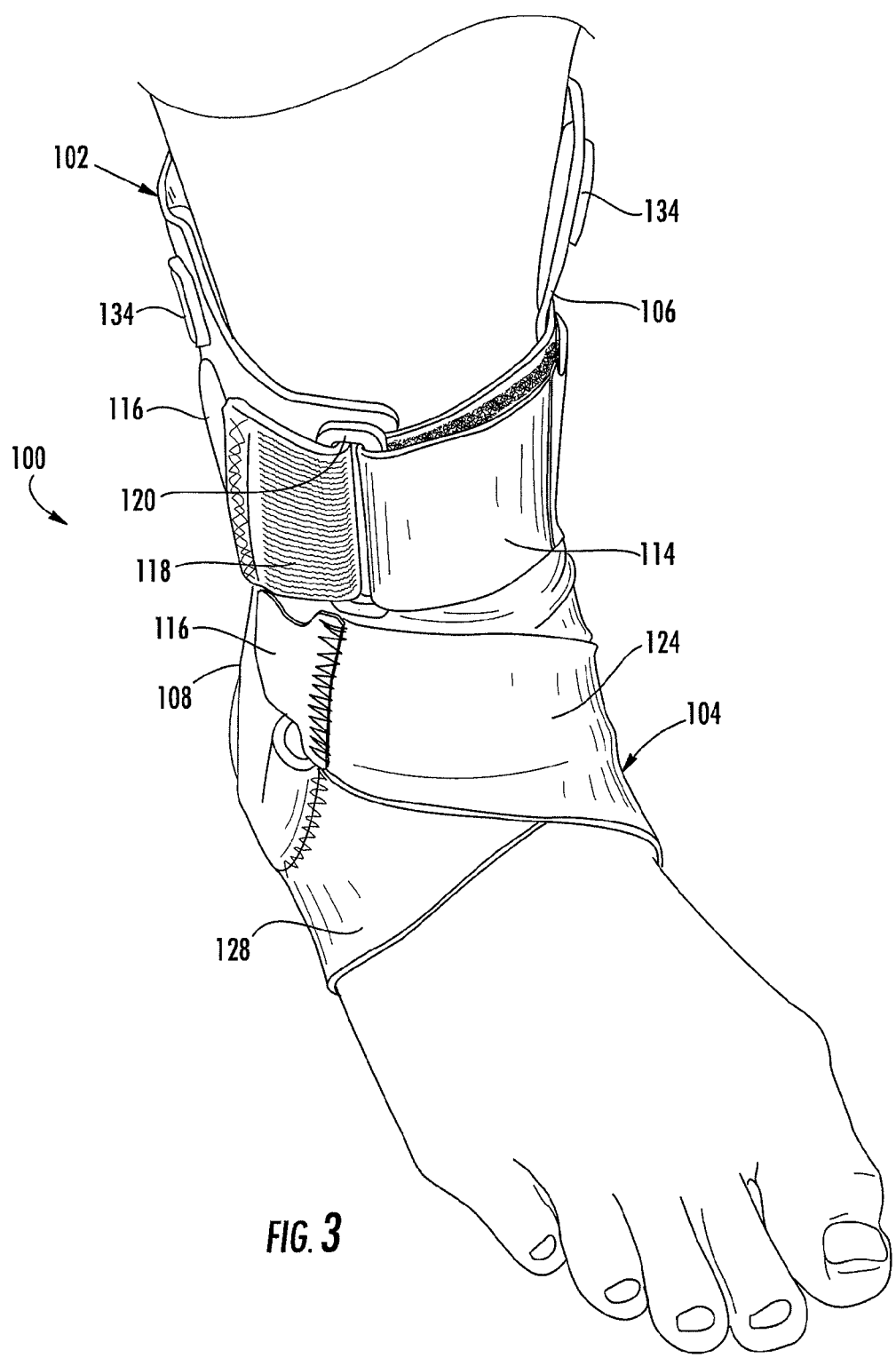
FIG. 3 is a perspective view of an ankle support positioned on a wearer's ankle, according to another embodiment of the present invention.

Referring now to the drawings and, in particular, to FIG. 1, there is shown a knee support 10. The knee support 10 is designed to wrap around a wearer's knee between the wearer's thigh and calf. The knee support 10 is adjustable with a plurality of straps that allow the knee support to be custom fitted depending on the size of the wearer's leg. In addition, the knee support 10 is easy to fit and remove, as the knee support is a generally planar structure that is wrapped around the wearer's leg instead of being pulled up the wearer's leg like a sleeve.

As shown in FIG. 1, the knee support 10 according to one embodiment of the present invention includes a sheet of material 12 constructed of a laminate material having multiple plies, including a soft, skin-friendly inner layer, a foam middle layer, and an outer layer. Advantageously, the inner layer is worn against the skin and has a low skin irritant, soft feel, and can have moisture-wicking properties, while portions of the outer layer allows attachment of complementary fastening material 34, as discussed below. For example, the sheet of material 12 could be a laminate of polyester hook engaging loop material, a polyurethane foam, and a polyester jersey knit material.

The sheet of material 12 includes opposing lateral edges 14, 16 and opposing top and bottom edges 18, 20, respectively. According to one embodiment, the area defined by the lateral ends and edges is approximately 10"×11", although the sizing may vary depending on the application and wearer of the knee support 10. However, it is preferred that the sheet of material 12, as defined above, remains generally rectangular or square in dimension. The lateral edge 16 is relatively flat or linear and intersects the top 18 and bottom 20 edges at approximate right angles. In one embodiment, the opposing top 18 and bottom 20 edges are substantially parallel to one another, although a slight taper occurs at a pair of integral straps 22, 24, as discussed below. The sheet of material 12 also defines a patellar opening 26 that is located generally in the center of the sheet of material. The patellar opening 26 is generally triangular with rounded corners, where the apex of the patellar opening extends distally when the opening is placed over a wearer's patella.

The knee support 10 includes a pair of laterally extending top and bottom straps 22, 24, respectively, that are integral with the sheet of material 12 and extend from the lateral edge 14 of the sheet of material. In one embodiment, each of the integral straps 22, 24 has a fastener tab 30 attached thereto. The fastener tab 30 preferably includes fastening material 34 on one surface for mating with complementary fastening material on the sheet of material 12. As mentioned above, the integral straps 22, 24 have a slightly tapering outer edge. The inner edge of the integral straps 22, 24 is also tapering or curved such that the straps define a gap 28 there between at the lateral edge 14 of the sheet of material 12. The gap 28 according to one embodiment of the present invention is about 4½ inches at the widest point. Furthermore, integral strap 22 may be slightly shorter than integral strap 24. In this regard, integral strap 24 is typically placed above the knee and about the wearer's thigh, while the shorter integral strap 22 is positioned below the knee and about the wearer's calf. In one embodiment, integral strap 22 is about 7½ inches in length measured from lateral edge 14, while integral strap 24 is about 8 inches in length.

The knee support 10 also includes a lateral edge strap 32 that extends from the lateral edge 16 of the sheet of material 12 in a direction opposite the integral straps 22, 24. The lateral edge strap 32 is positioned approximately midway between the top 18 and bottom 20 edges such that the lateral edge strap is capable of wrapping behind a wearer's knee and overlapping the lateral edge 14 in the gap 28 defined by the upper and lower integral straps. Unlike the integral straps 22, 24, the lateral edge strap 32 is attached to the sheet of material 12 with stitching. The lateral edge strap 32 of the knee support 10 includes a fastener tab 30 attached to its free end. In one embodiment, the lateral edge strap 32 is approximately 6½ inches in length measured from the lateral edge 16.

The aforementioned features of the knee support 10 are not meant to be limiting, as there may be many modifications in alternative embodiments of the present invention. For instance, there may be any number of integral 22, 24 and lateral edge 32 straps in various embodiments of the present invention to provide a range of support for the wearer. Thus, there could be one or more integral straps 22, 24 defined along the lateral edge 14, and one or more lateral edge straps 32 defined along the lateral edge 16. Furthermore, each of the integral 22, 24 and lateral edge 32 straps may be various sizes and configurations for accommodating different sizes of wearers. For example, although the lateral edge strap 32 is shown as being formed of a separate material and affixed to the sheet of material 12, the lateral edge strap could be formed integral with the sheet of material.

An outer surface of the sheet of material 12 includes a fastening material that is complementary to fastening material 34 carried by the fastener tabs 30. Typically, the fastening material 34 of the fastener tabs 30, as well as the fastening material on the outer surface of the sheet of material 12, are constructed of a complementary hook and loop material such as VELCRO®. However, the term "fastening material," as used herein, denotes any type of chemical, mechanical, or other fastener that allows connection of two separate components, such as snaps, hook and loop connectors, adhesives, buckles, etc. Notably, the fastening material 34 of the fastener tabs 30 (e.g., hooks), and the fastening material (e.g., loops) of the outer surface of the sheet of material 12 mate to, and attach with, one another when brought into contact. These fastening materials, therefore, are referred to herein as being complementary.

Supporting the opposite surface of the fastening material 34 are the fastener tabs 30, which are preferably made from a flexible polymeric support. The fastening material 34 is attached to the fastener tabs 30 via injection molding or with an adhesive or similar attachment technique. Therefore, the fastener tab 30 provides increased support and durability for the fastener tabs 30.

The fastener tabs 30 could be a polymeric material, such as polyethylene, and formed by injection molding or compression molding. The fastener tabs 30 could be attached to the straps with various techniques or a combination of techniques, such as with an adhesive, stitching, RF welding, etc., but would preferably be attached using a combination of an adhesive applied to the fastener tabs 30 and/or fastening material 34 and RF welding the fastener tabs and/or fastening material to a respective strap along the adhesive. A combination of adhesives and RF welding reduces the assembly time typically required to secure a fastener to a respective strap, which is generally performed using stitching. In one aspect of the present invention, the fastener tabs 30 are secured to a respective strap by injection molding the polymeric support directly to the integral 22, 24 and lateral edge 32 straps. Furthermore, the fastening material 34 could also be formed integrally with the fastener tab 30, such as by injection molding.

The knee support 10 may include various additional features. For example, the knee support 10 may include an inflatable bladder having a depressible pump 50 and release valve 56 for selectively inflating and deflating the inflatable bladder. For a further discussion of an exemplary inflatable bladder, see U.S. patent application Ser. No. 11/609,095, entitled "Edge Binding for Orthopedic Supports and Method of Using Same," which is assigned to the present assignee and incorporated herein by reference. The knee support 10 may also include a plurality of stays 58 secured to the sheet of material 12 for supporting the medial and lateral sides of the knee. See U.S. patent application Ser. No. 11/609,105, entitled "Stay Hinge for Orthopedic Supports and Method of Using Same," which is assigned to the present assignee and incorporated herein by reference, for an exemplary discussion of stays 58 that could be utilized with the knee support 10.

The knee support 10 is applied to a wearer's knee area by positioning the support such that the patella registers with the patellar opening 26, and then wrapping the integral straps 22, 24 about the wearer's leg such that the upper strap 24 is positioned above the popliteal region of the knee and attaches to the sheet of material 12, and the lower strap 22 is positioned below the popliteal region and attaches to the sheet of material. The lateral edge strap 32 is then wrapped behind the knee until the fastener tab 30 of the lateral edge strap overlaps lateral edge 14 and is secured to the complementary fastening material on the outer surface of the sheet of material 12. In this regard, the fastening material 34 of the integral straps 22, 24 can be adjusted to the wearer's leg size by releasably securing the fastening material to the outer surface of the sheet of material 12. When properly positioned, the inflatable bladder 34 provides cushioning and support about the wearer's patella. The flexible stays 58 provide bending resistance with flexion of the knee and medial/lateral support in order to support the knee area and prevent excessive movement thereof. Furthermore, the inflatable bladder 34 may be inflated or deflated to a desired pressure to provide cushioning and support on an opposite surface of the flexible stays.

Ankle Support

Another embodiment of the present invention provides an ankle support 100, which is depicted in FIGS. 3-8. In general, the ankle support 100 includes ankle portion 102 that is configured to extend about portions of the wearer's foot and lower leg to enclose the wearer's ankle. The ankle support 100 includes a strapping system 104 for securing the sheet of material to the wearer's ankle for supporting the ankle.

Figure 4:
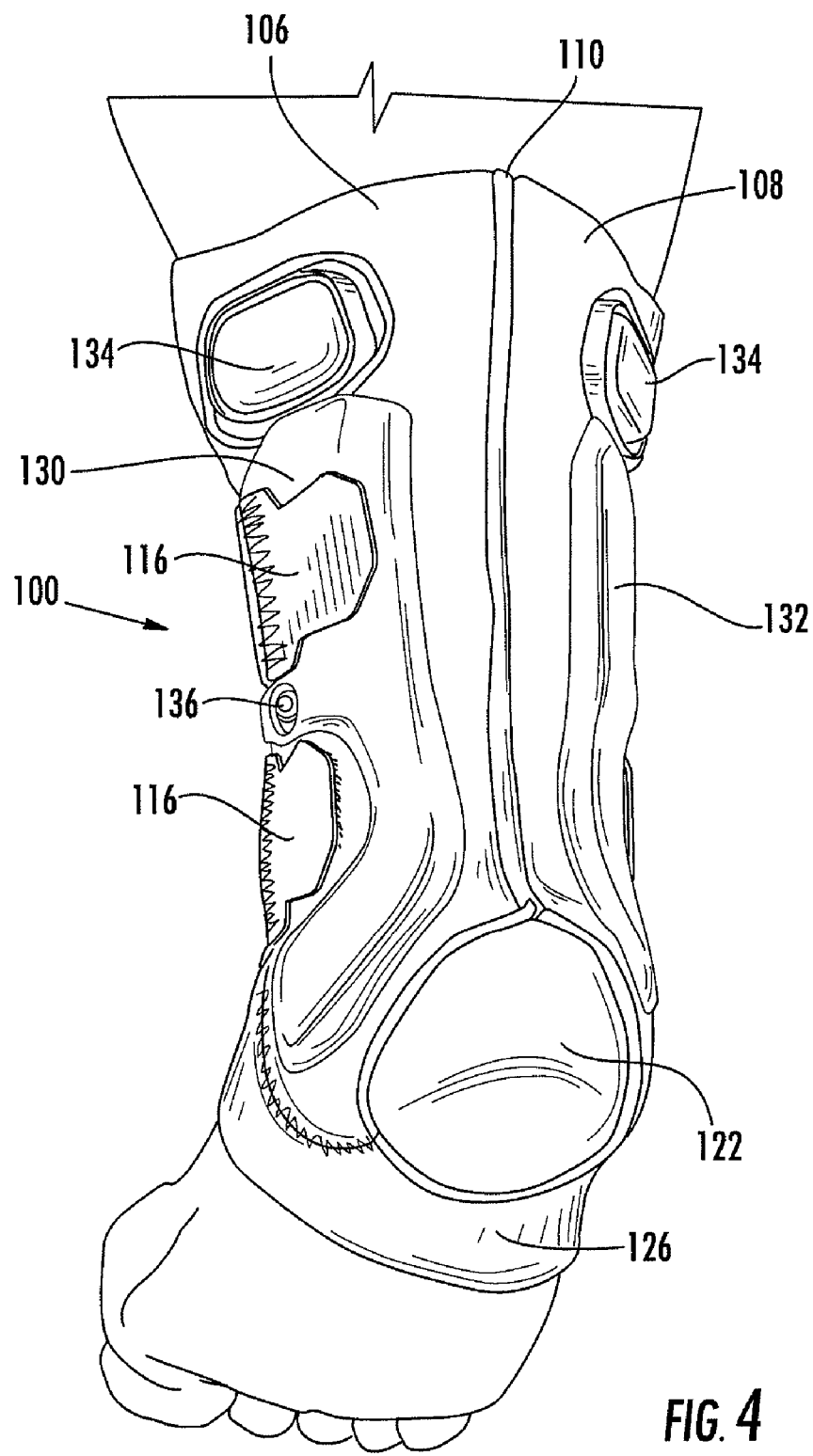
FIG. 4 is another perspective view of the ankle support shown in FIG. 3.

Generally, the ankle support 100 includes an ankle portion 102 and a strapping system 104 each manufactured from a sheet of soft and flexible laminate material. The laminate material is typically a laminate of polyester, polyurethane foam, and polyester. The ankle portion 102 includes a medial portion 106 and a lateral portion 108 (note that the ankle support is ambidextrous and reference to the medial and lateral portions are for illustrative purposes only, as the ankle support may be worn on either the right or left ankle) that are attached along a lateral edge, such as with stitching 110. As shown in FIG. 4, the stitching 110 is located approximately along the posterior of a wearer's lower leg and ankle when the ankle support 100 is worn. For an exemplary discussion of an ankle portion 102 and strapping system 104, see U.S. Pat. No. 6,929,617, entitled "Nonbulky Ankle Brace for Use with Footwear," which is assigned to the present assignee and incorporated herein by reference.

Figure 5:
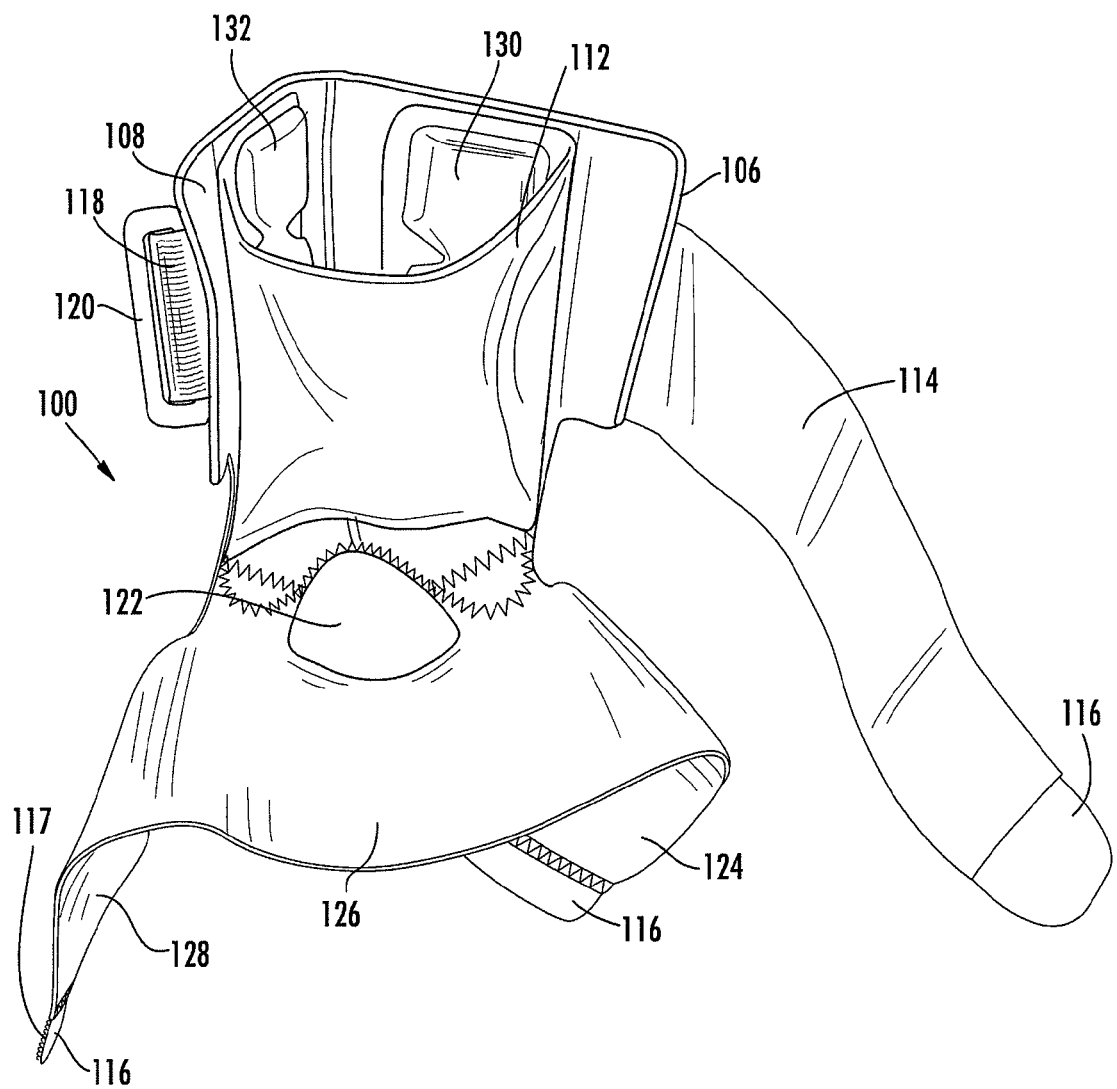
FIG. 5 is a perspective view of the ankle support shown in FIG. 1 removed from the wearer's ankle.

A backing material 112 is secured to the inner surface of the medial 106 and lateral 108 portions and extends between lateral edges of the ankle portion to form a sleeve, as shown in FIG. 5. The sleeve aids in initially positioning the ankle support 100 on the wearer's ankle, as well as providing additional comfort for the wearer. As such, the backing material 112 is stretchable and conformable to a variety of ankle sizes and is typically a polyester or polyester/spandex material.

A substantially non-stretchable strap 114 is attached to the medial portion 106 at one end and has a fastener tab 116 at its free end. Optionally, a small tab 118 extends outwardly from the lateral portion 106 where a ring 120 is attached thereto. Thus, the non-stretchable strap 114 may engage the ring 120 and loop over and attach to the outer surface of the non-stretchable strap or the ankle portion 102 to restrain the ankle support 100 about the wearer's shin.

The strapping system 104 is attached to each of the medial 106 and lateral 108 portions to define an opening 122 for the wearer's heel. The strapping system 104 includes a single strip of material having a medial strap 124, a base 126, and a lateral strap 128. The base 126 is positioned adjacent to the bottom of a wearer's foot, while the medial 124 and lateral 128 straps may cross one over one another to attach to the outer surface of the lateral 108 and medial 106 portions, respectively. In this regard, each of the medial 124 and lateral 128 straps includes a fastener tab 116 having a fastening material 117 that may attach to a fastening material on the outer surface of the ankle portion 102.

Each of the medial 106 and lateral 108 portions have respective medial 130 and lateral 132 bladders attached thereto (a profile of a portion of the bladders is shown in FIGS. 4 and 5). A stay (not shown) is positioned adjacent to each of the medial 130 and lateral 132 bladders such that the stays are restrained between the bladders and the sheet of laminate material of the ankle portion 102. The medial 130 and lateral 132 bladders are positioned between the backing material 112 and sheet of laminate material such that the bladders are located adjacent to the wearer's skin when the ankle support 100 is worn. The medial 130 and lateral 132 bladders generally extend along the entire length of the respective medial 106 and lateral 108 portions, where each bladder includes a pump 134 that is accessible to a wearer when the ankle support 100 is worn. As shown in FIG. 4, openings are defined in the outer surface of each of the medial 106 and lateral 108 portions that expose each pump 134. Approximate a midpoint of the medial 130 and lateral 132 bladders is a release valve 136, where openings are also defined in the laminate sheet of material to facilitate accessibility of the release valves.

The medial 130 and lateral 132 bladders operate in the same manner as that of the knee support. Thus, the medial 130 and lateral 132 bladders are inflated by depressing the pump 134, while air may be released from the bladders by depressing the release valve 136. Although not shown, a portion of each of the medial 130 and lateral 132 bladders includes a plurality of longitudinal channels extending from the pump 134 and approximately to the release valve 136. The remaining portion of the medial 130 and lateral 132 bladders extends from about a respective release valve 136 and downwardly to a generally L-shaped bottom portion, as shown in FIG. 4. Thus, the bladders extend over a portion of the lower leg, ankle, and foot of a wearer. Similarly, each stay has a substantially similar configuration as that of the medial 130 and lateral 132 bladders. The stays are typically a thin plastic material that aid in medial and lateral stability.

Various techniques could be employed to assemble the ankle support 100. For example, RF welding could be employed to secure the medial 130 and lateral 132 bladders to respective medial 106 and lateral 108 portions. In addition, the backing material 112 may be attached to the ankle portion 102 with RF welding. Typically, the backing material 112 is attached to the ankle portion 102 by simultaneously RF welding the backing material around the edges of the medial 130 and lateral 132 bladders and to the inner surface of the ankle portion. As such, the bladders serve as an adhesive to secure the backing material 122 to the medial 106 and lateral 108 portions.

It is understood that that ankle portion 102 and strapping system 104 may be various configurations to achieve a desired amount of support and comfort. For example, the non-stretchable strap 114 could be various sizes and materials and, in one aspect, may be a stretchable material. In addition, although the strapping system 104 is described as being a single piece of material, the strapping could be separate pieces of material if desired. Similarly, although the medial 106 and lateral 108 portions are shown as separate sheet of material, the medial and lateral portions could be integrally formed from a single sheet of material. Furthermore, there could be no bladders and/or stays to achieve a desired amount of support, as well as variety of sizes and configurations of bladders and stays.

Figure 6:
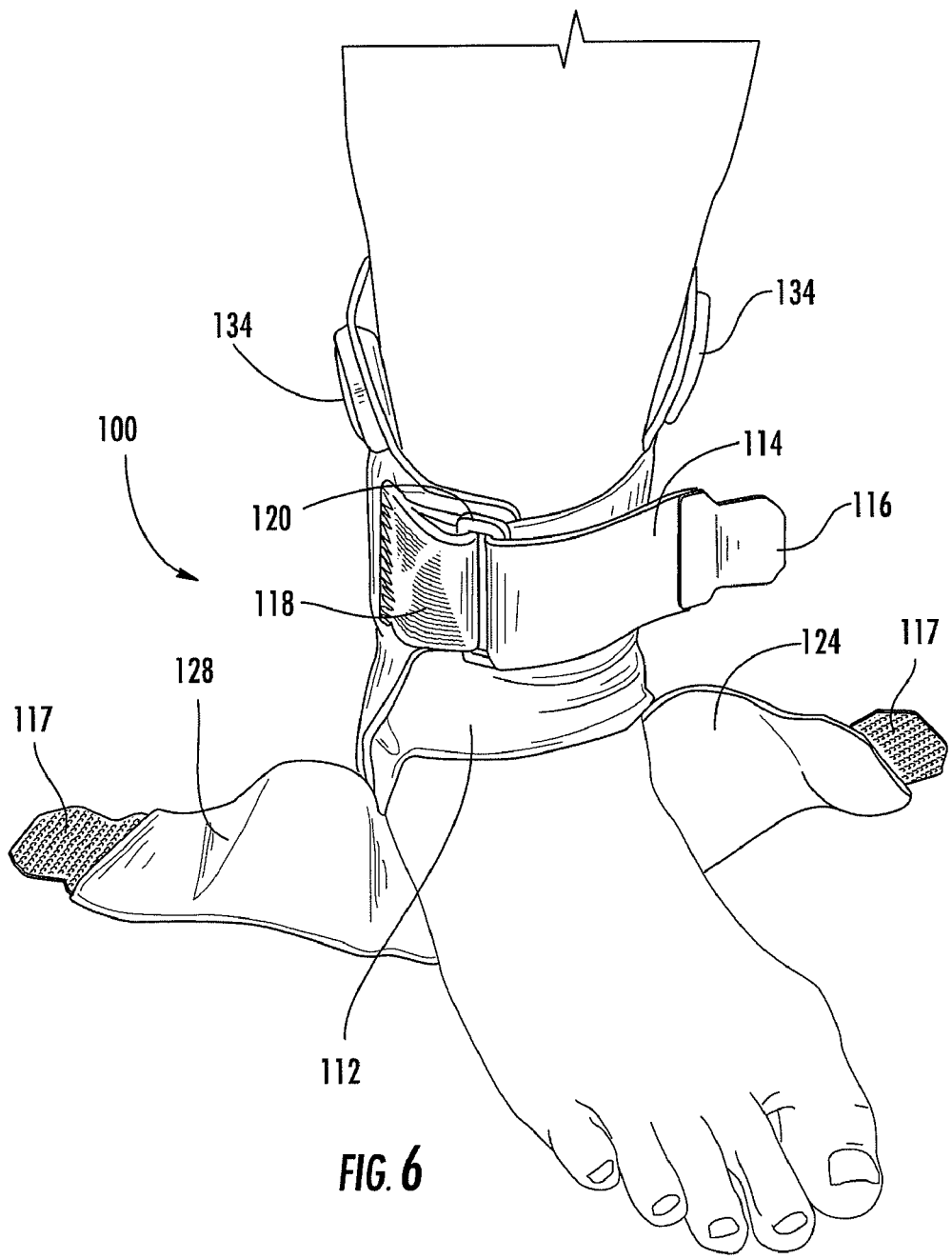
FIGS. 6-8 are perspective views of a sequence of securing the ankle support to a wearer's ankle according to one embodiment of the present invention.
Figure 8:
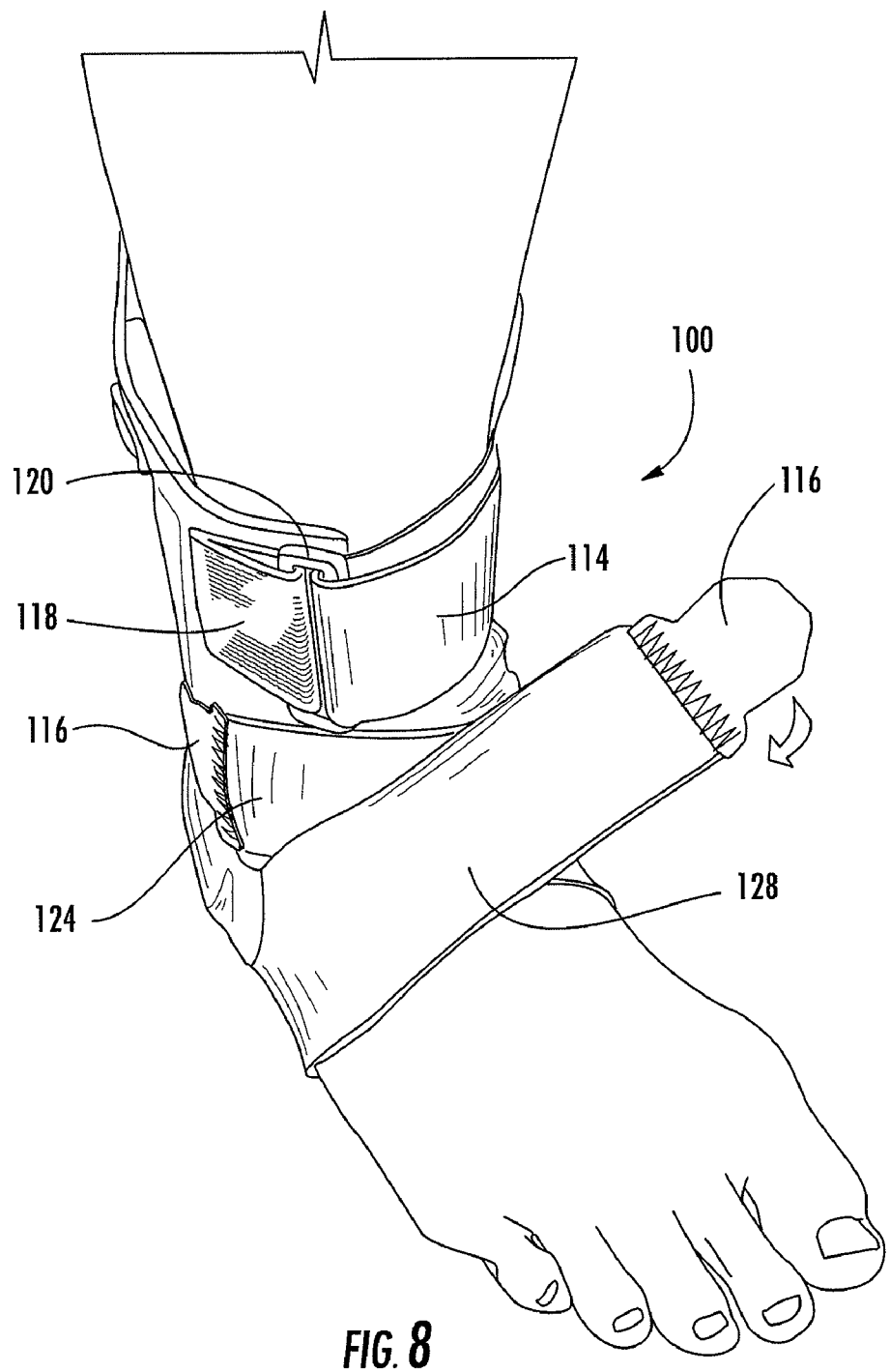

Similar to the fastener tabs 30 described above for the knee brace, the fastener tab 116 is a flexible polymeric support that is located on the opposite surface of fastening material 117, such as hook material. Thus, the fastening material 117 could be attached to the fastener tab 116 via injection molding or with an adhesive or similar attachment technique. The fastener tab 116 and fastening material 117 may flare outwardly at its respective base to provide a broader surface area of attachment to a respective strap. For example, FIGS. 6 and 8 illustrate that the base of the fastener tab 116 flares outwardly along a free end of a respective strap such that a portion of the base of the fastener tab is attached to a portion of a respective strap.

The fastener tabs 116 may comprise various sizes and configurations. For example, the fastener tabs 116 could have rounded corners in a semi-circular shape, as opposed to having beveled corners. In addition, the fastener tabs 116 could be various shapes, such as rectangular, and provide adequate surface area to support the fastening material 117 and to promote attachment to complementary fastening material. Furthermore, the fastener tabs 116 may be various sizes depending on the type and size of strap, the amount of force required to secure the fastener tabs and/or fastening material to a respective strap or complementary fastening material, and/or the location of the fastening tab and strap on the wearer's anatomy.

The fastener tab 116 is preferably a polymeric material, such as polyethylene, that is formed by injection molding or compression molding. In one aspect of the present invention, the fastener tabs 116 are secured to a respective strap by injection molding the polymeric support directly to the medial 124 and lateral 128 straps. However, the fastener tabs 117 could be attached with similar techniques or combination of techniques, such as with an adhesive, stitching, RF welding, etc. Furthermore, the fastening material 117 could also be formed integrally with the fastener tab 116, such as by injection molding.

Figure 7:
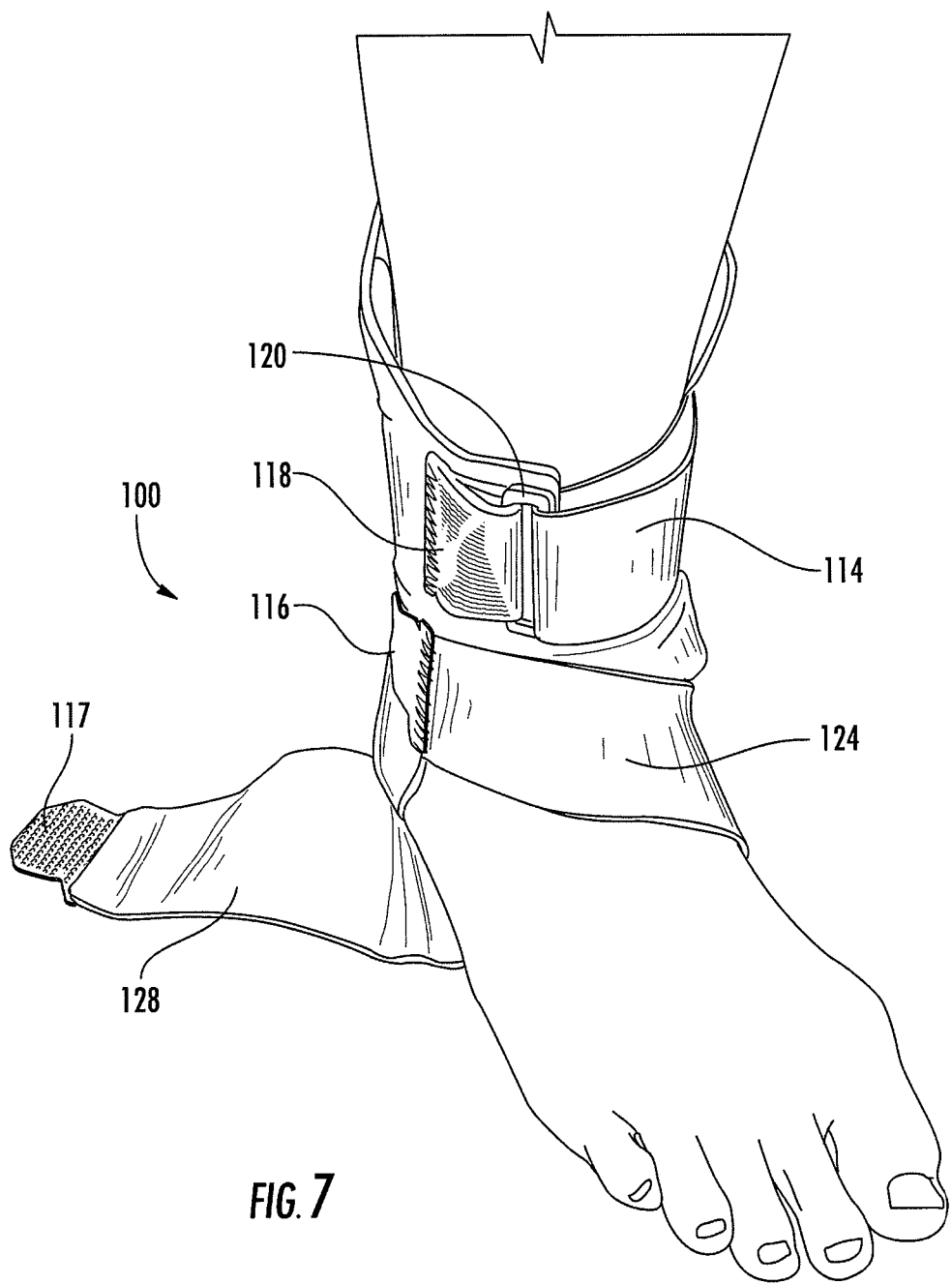

During use, the wearer pulls apart the opposing edges of the ankle portion 102 to the configuration illustrated in FIG. 5, and slides his or her foot into the sleeve until the wearer's heel extends through the heel opening 122. Meanwhile the ankle portion 102 is pulled up onto about the mid-point of the lower leg or a portion of the wearer's calf. The medial 124 and lateral 128 straps are crossed over each other at the instep and anterior portion of the ankle. The straps are pulled tight and the fastening material 117 at the end of each of the straps is attached to the fastening material on the medial 106 or lateral 108 portions of the ankle portion 102 opposite from the side of the base 126 on which the respective strap originated (FIGS. 7 and 8). At the top of the ankle portion 102, the free end of the non-stretchable strap 114 is threaded outwards through the ring 120 attached to the small tab 118 and wrapped back on itself. The non-stretchable strap 114 is extended around the ankle portion 102, pulled tight to hold the edges of the ankle portion together, and the fastening material 117 on its free end is secured to the adjacent fastening material on the outer surface of the ankle portion (FIG. 6). It is understood that the sequence of securing the ankle support 100 on the lower leg and foot is not meant to be limiting. For example, the non-stretchable strap 114 could be initially secured and the medial 124 and lateral 128 straps secured thereafter if desired.

Wrist Support

An additional embodiment of the present invention provides a wrist support, as shown in FIGS. 9-16. The wrist support 200 generally includes a sheet of material 202 that is configured for wrapping about portions of a wearer's hand and forearm to enclose the wearer's wrist. The wrist support 200 also includes a strapping system for securing the sheet of material 202 about the wearer's wrist. The strapping system may be used to maintain the wrist support 200 in a ready-to-wear configuration, such that the support may be readily positioned and secured on the wearer's wrist.

The sheet of material 202 is a flexible and soft laminate material that provides moisture wicking and cushioning properties. For example, the laminate material could be a laminate of polyester, polyurethane foam, and polyester. The wrist support 200 shown would typically be worn on a right hand of a wearer, although the wrist support could be configured to be worn on a left hand if desired. The sheet of material 202 includes a proximal edge 204, a distal edge 206, and a pair of opposing lateral edges 223 and 227 extending there between. The proximal edge 204 is substantially linear, while the distal edge 206 includes a curvature that arcs proximate to a thumb hole 212, as shown in FIGS. 11 and 12.

Figure 11:
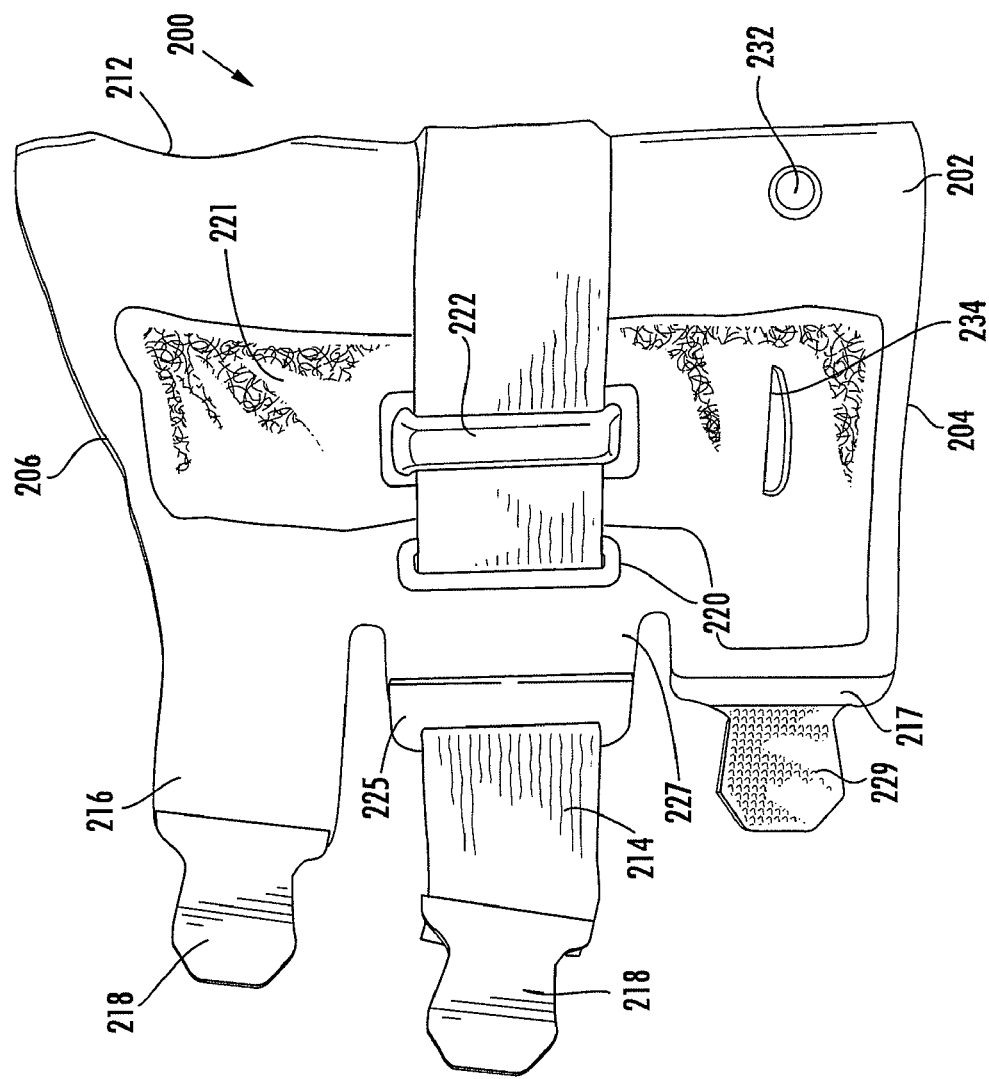
FIG. 11 is a plan view of the palmar side of the wrist support shown in FIGS. 9 and 10 removed from the wearer's wrist.
Figure 12:
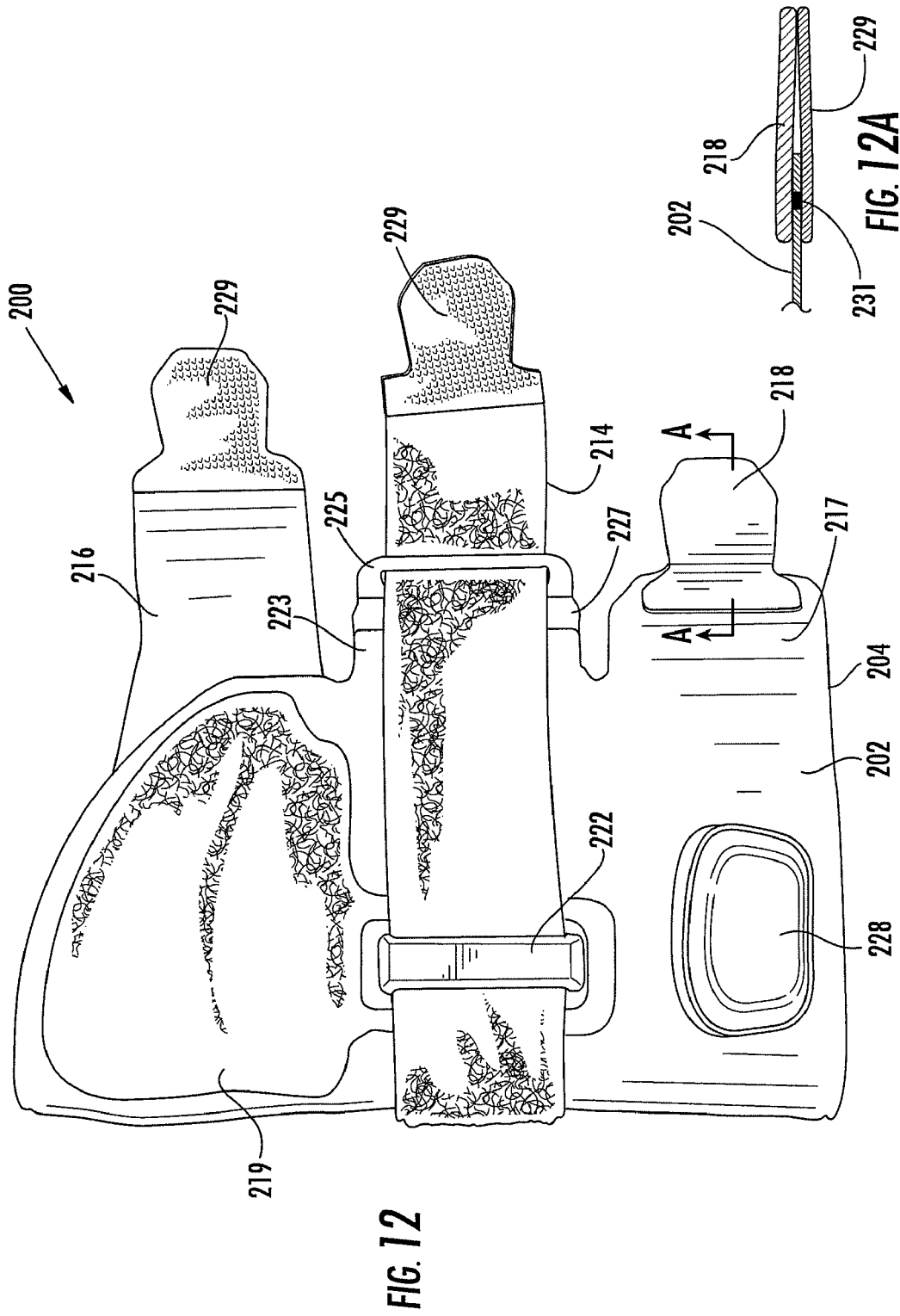
FIG. 12 is a plan view of the dorsal side of the wrist support shown in FIGS. 9 and 10 removed from the wearer's wrist.

One lateral edge includes a longitudinal strap 214 positioned between the proximal 204 and distal 206 edges, as well as a strap 217 having a portion extending along the proximal edge 204 (see FIG. 12). Further, the opposite lateral edge includes a strap 216 having a portion extending along the distal edge 206 (see FIG. 11). Thus, the straps 216 and 217 are integral with the sheet of the material 202, although the straps could be attached to respective lateral edges 227 and 223 of the sheet of material 202 if desired.

The longitudinal strap 214 attaches to a first lateral edge 223 and extends through a pass 220 defined in the sheet of material 202 (see FIG. 11). The longitudinal strap 214 is capable of wrapping circumferentially about the wearer's wrist and through a pair of strap guides 222 secured to the outer surface of the sheet of material 202. The longitudinal strap 214 further extends through a ring 225 attached to a second lateral edge 227 such that the strap may loop back over itself, and the fastening material 229 may attach to complementary fastening material on the outer surface of the longitudinal strap.

The strap 217 typically encircles a portion of the wearer's forearm so that the fastening material 229 attaches to a longitudinal patch 221 of fastening material. Similarly, the strap 216 includes a fastening material 229 on its free end and may encircle about a portion of a wearer's palm and attach on a patch 219 of fastening material. As such, the cooperation of the straps 214, 216, and 217 secure the sheet of material 202 to the wearer's hand, wrist, and forearm.

The pass 220 is preferably a polymeric material that extends through the thickness of the sheet of material 202 and attaches to the sheet of material about the outer periphery of the pass. Thus, the opening defined in the pass 220 allows the longitudinal strap 214 to pass therethrough, as well as slide therein. The pass 220 is generally configured to have a slightly larger cross section than the longitudinal strap 214 to facilitate sliding of the strap therein. The strap guides 222 also provide openings to allow the longitudinal strap 214 to slide therein and provide guides for properly positioning the longitudinal strap about the wearer's wrist. In particular, each strap guide 222 includes a base and a raised U-shaped member attached to the base, where the U-shaped member includes an opening for receiving the longitudinal strap 214. The pass 220 is typically injection molded about an opening defined in the sheet of material 202, while the strap guides 222 are typically injection molded to the outer surface of the sheet. In this regard, an opening is formed in the sheet of material 202 before injecting polymeric material about the edges of the opening to form the pass 220.

It is understood that the pass 220 and strap guides 222 may be various sizes and configurations in various aspects of the present invention. For example, although only a pair of strap guides 222 is illustrated, there could be at least one strap guide attached to the outer surface of the sheet of material 202 if desired. In addition, the pass 220 and strap guides 222 could be secured to the sheet of material 202 using various techniques, such as with an adhesive. The pass 220 and strap guides 222 may also comprise various configurations to enable straps of various sizes and configurations to fit and slide therethrough. For example, the pass 220 and strap guides 222 could include a circular opening to accommodate a longitudinal strap 214 having a circular cross section. The pass and strap guides are preferably polymeric materials such as, for example, polyethylene, polyester, polyurethane, or combinations thereof.

As described above with respect to the knee and ankle supports, each fastener tab 218, which is located on the opposite surface of respective fastening material 229, is typically a flexible polymeric support. Thus, the fastening material 229 is attached to the fastener tab 218 via injection molding or with an adhesive or similar attachment technique. The fastener tab 218 is preferably a polymeric material such as, for example, polyethylene, polyester, polyurethane, or combinations thereof, that is formed by injection molding or compression molding. As described above with respect to the ankle support 100, the fastener tab 218 and fastening material 229 may flare outwardly at its respective base to provide a broader surface area of attachment to a respective strap.

Furthermore, each fastener tab 218 may include one or more prongs 231, as shown in FIG. 12A. The prong 231 may be integrally formed with a respective fastener tab 218 and extend outwardly therefrom and engage an opening formed in a respective strap. Thus, the prong 231 provides additional support for attaching the fastener tab 218 to a respective strap and/or fastening material 229. Moreover, FIG. 12A demonstrates that the fastener tab 218 and fastening material 229 may slightly overlap a free end of a respective strap. Thus, at least a portion of each of the fastener tab 218 and fastening material 229 is separately attached to a respective strap.

In one aspect of the present invention, the fastener tabs 218 are secured to respective straps 214, 216, and 217 by injection molding. However, the fastener tabs 218 could be attached with similar techniques or combination of techniques, such as with an adhesive, stitching, RF welding, etc. Furthermore, the fastening material 229 could be formed integrally with the fastener tab 218, such as by injection molding.

The wrist support 200 also includes a pump 228 that is in fluid communication with a bladder (not shown) that operates in a similar manner as that described above for the knee 10 and ankle 100 supports. The bladder includes a protuberance that is adjacent to the strap guide 222 located proximate to the pump (i.e., the dorsal side of the wearer's wrist according to the wrist support 200 shown in FIGS. 10 and 12), as well as a plurality of channels located distally of the strap guide. The bladder includes a protuberance located proximate to the proximal end of the palmar stay, as well as a protuberance located distally and positioned to fit within the palm of the wearer. A conduit (not shown) extends between the pump 228, a release valve 232, and the bladder such that the conduit carries air supplied by the pump.

An opening is defined in the sheet of material 202 such that the pump 228 is positioned adjacent to the outer surface of the sheet of material and is in fluid communication with the bladder. A small hole is also defined in the sheet of material 202 such that the release valve 232 is accessible by a wearer. A slot 234 is defined in the patch 221 to allow the insertion of a palmar stay between the patch and the outer surface of the sheet of material 202. Thus, when the wrist support 200 is positioned on the wearer's wrist, portions of the bladder are positioned adjacent to the stay and to the wearer's skin. The palmar stay typically includes a curvature that conforms to the wrist and palm of the wearer. Furthermore, a slot 234 may be defined in the patch 219 of fastening material for receiving a dorsal stay (not shown). As such, one or more stays may be employed with the wrist support 200 to increase stability.

The palmar bladder may be secured to an inner surface of the sheet of material 202 using various techniques such as RF welding. In particular, a backing material, typically a polyester material, is sized and configured to the outer periphery of the sheet of material 202 and is RF welded thereabout with an adhesive that is pre-applied to the backing material. The backing material is also RF welded at various locations about the outer periphery of the bladder using portions of the bladder as an adhesive to prevent the bladder from moving out of position. However, various techniques could be employed to secure the backing material to the sheet of material 202, such as with stitching.

Figure 9:
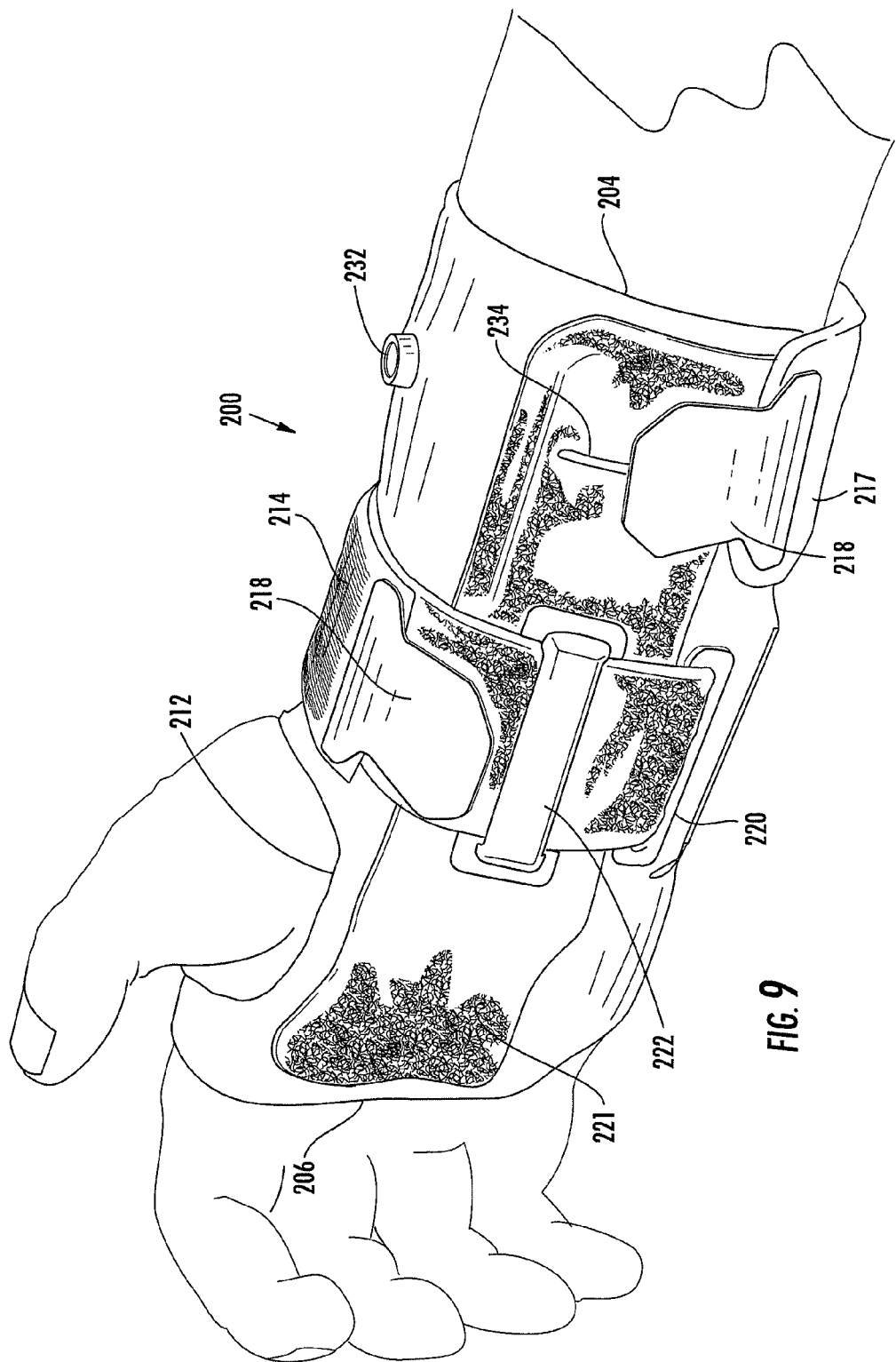
FIG. 9 is a perspective view of a palmar side of a wrist support according to an additional embodiment of the present invention.
Figure 10:
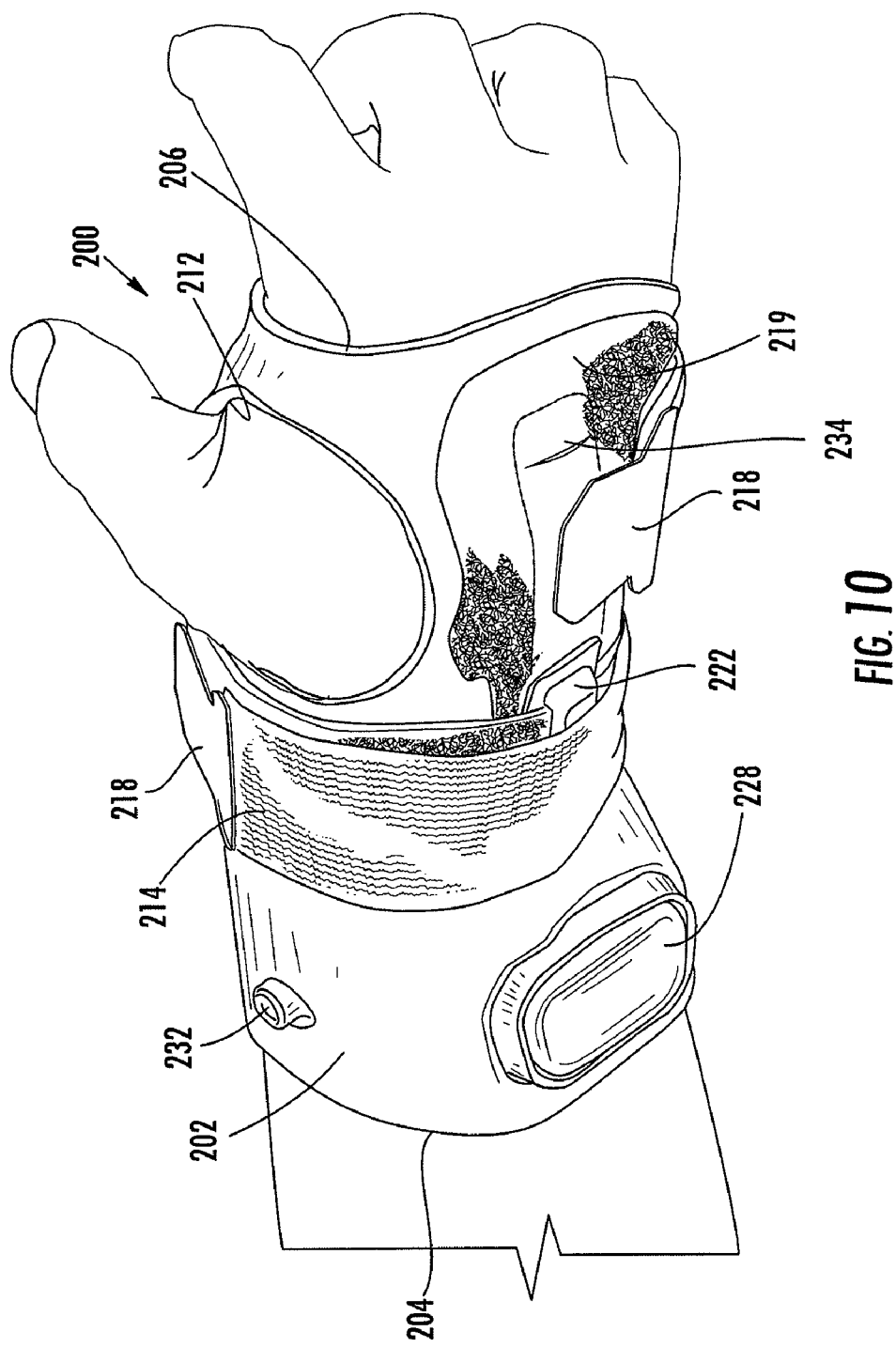
FIG. 10 is a perspective view of a dorsal side of the wrist support shown in FIG. 9.
Figure 13:
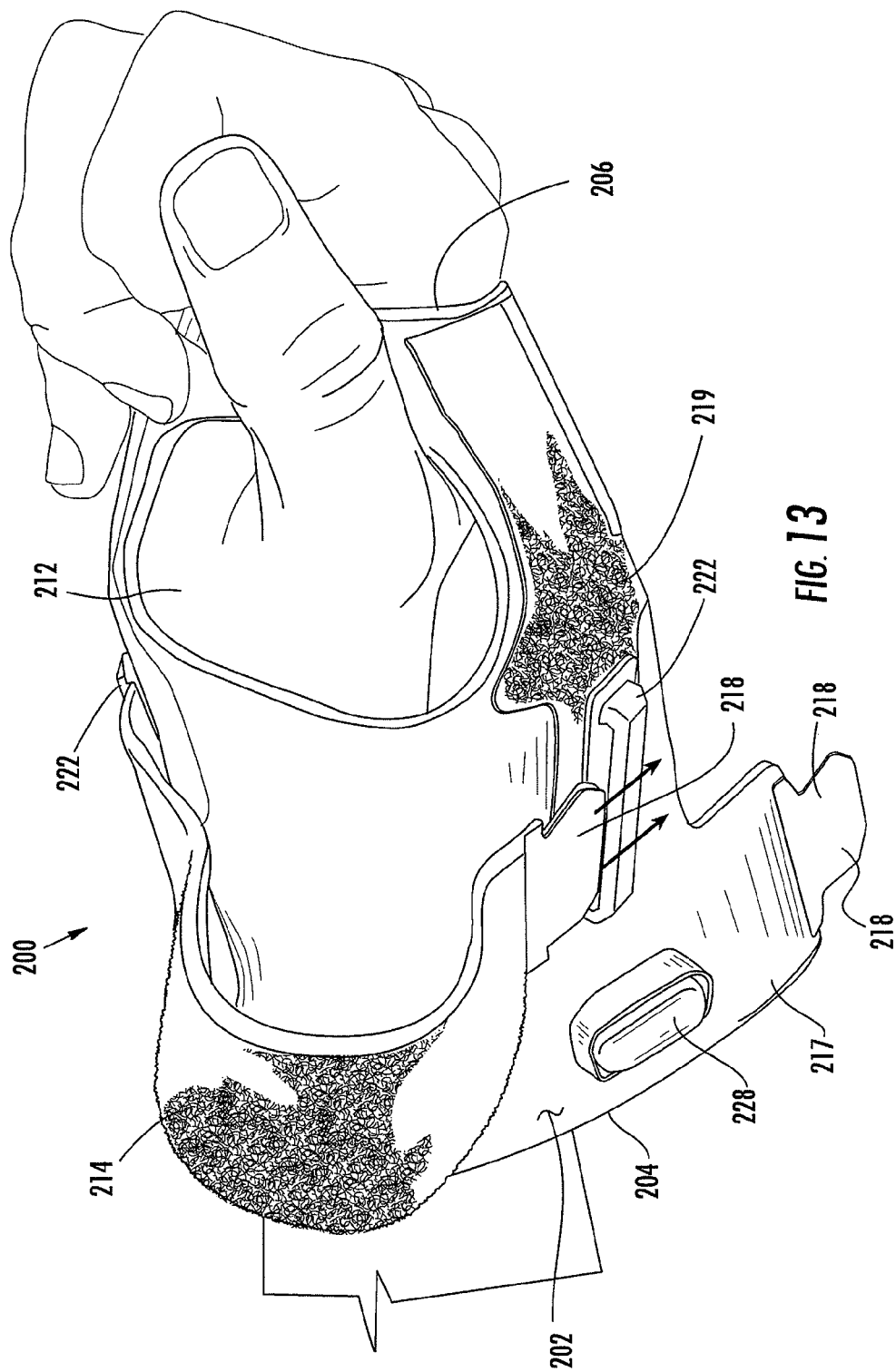
Figure 14:
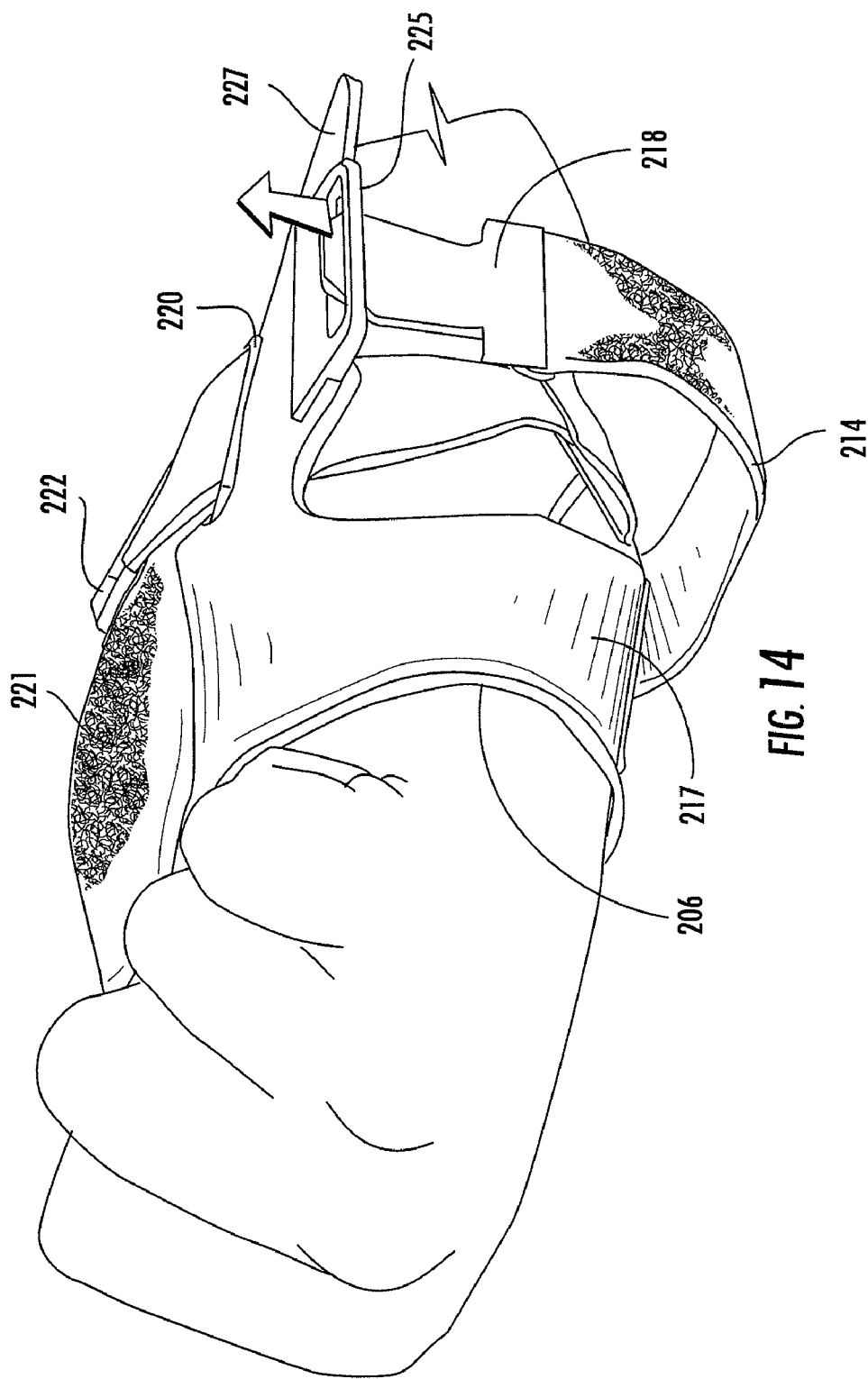
Figure 15:
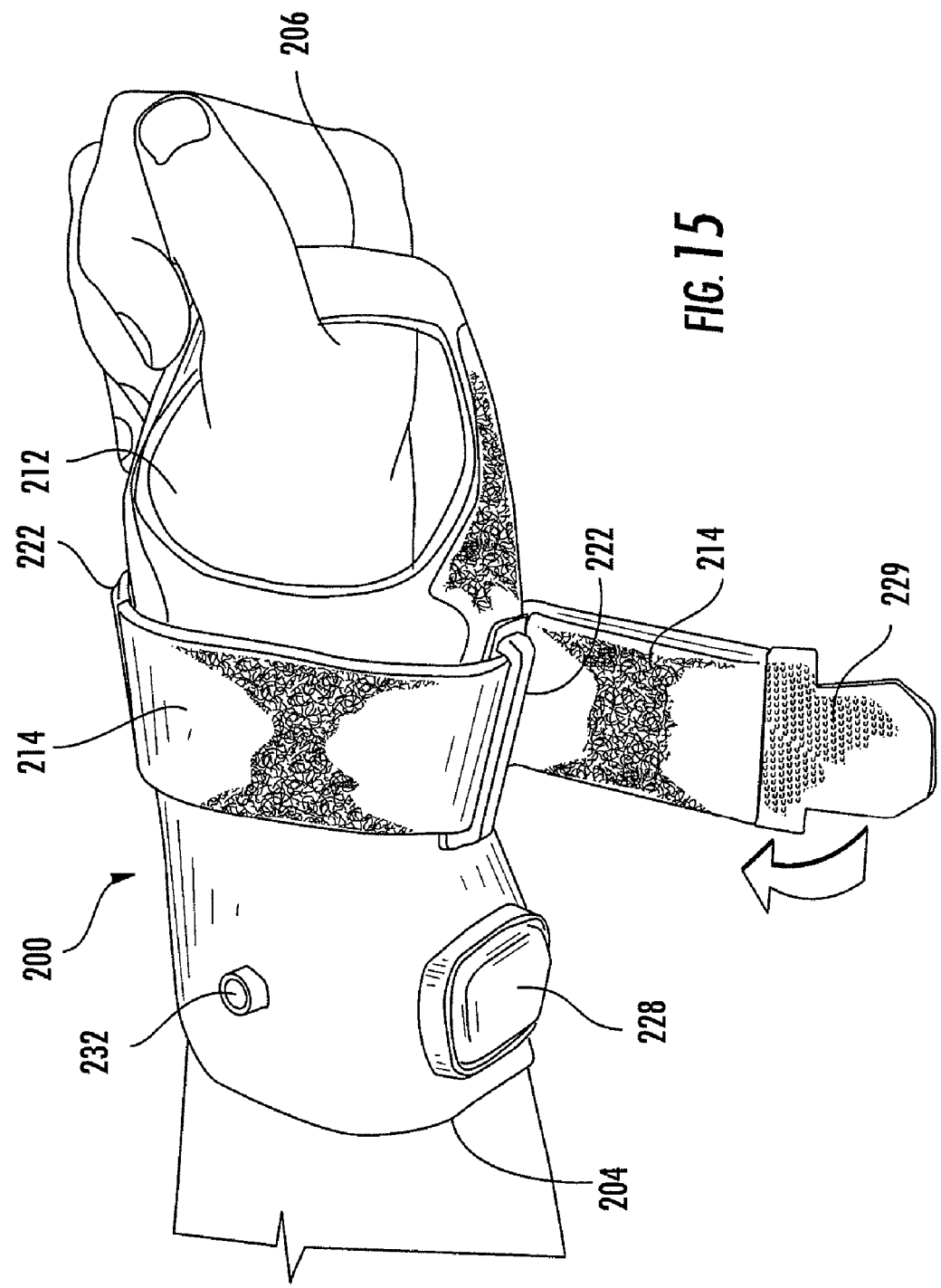

To secure the wrist support 200 to a wearer's wrist, the wearer initially positions his or her wrist such that the wearer's thumb extends through the thumb hole 212, and the wearer's fingers extend distally from the distal edge 206. In addition, if a palmar stay is utilized, the distal end of the palmar stay would be positioned within the wearer's palm, while the remaining portion of the palmar stay would extend proximally along the wrist and forearm of the wearer. The longitudinal strap 214 is positioned through the strap guides 222 and wrapped circumferentially about the wearer's wrist, as shown in FIG. 13. The wearer may then loop the longitudinal strap 214 through the ring 225, as shown in FIG. 14, and back over itself, as shown in FIG. 15. Thus, the longitudinal strap 214 is wrapped back to overlap itself as the strap is wrapped circumferentially about the wearer's wrist. The longitudinal strap 214 may then be tensioned and secured to itself, as illustrated in FIG. 16. However, the longitudinal strap 214 could be arranged such that strap is initially positioned through the strap guides 222 and ring 225 prior to positioning the wearer's hand in the wrist support 200. Thus, the wrist support 200 would be in a "ready-to-use" configuration that allows the wearer to easily position and secure the wrist support to the wearer's hand, wrist, and forearm. Moreover, FIG. 16 demonstrates that the straps 216 and 217 may be tensioned and attached to respective patches of fastening material 219 and 221. FIG. 9 depicts the wrist support 200 properly positioned and secured on a wearer's wrist.

Embodiments of the present invention may provide many advantages. For instance, the fastener tabs may provide increased support and durability to the fastening material attached to its opposite surface without increasing the incidence of irritation to the wearer's skin or clothing. The fastener tabs are typically a polymeric material that may be easily fabricated and assembled to the fastening material and/or sheet of material. In addition, the strapping configuration of the orthopedic support provides a "ready-to-use" configuration that enables a wearer to initially position the support on the wearer's limb and further secure the support thereon. The strapping system provides components (e.g., the strap guide, pass, and ring) that may be easily manufactured and assembled to the sheet of material. Furthermore, the fastener tabs and strapping system are also capable of being used with a variety of orthopedic supports, including the knee, ankle, and wrist.

Many modifications and other embodiments of the invention set forth herein will come to mind to one skilled in the art to which this invention pertains having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. An orthopedic support comprising:
   a sheet of material that is flexible and configured to extend around a wrist of a wearer, the sheet of material comprising a pair of opposing lateral edges;
   at least one longitudinal strap attached to one of the opposing lateral edges of the sheet of material;
   at least one fastener tab secured to a free end of the at least one strap;
   at least one pass attached within the sheet of material proximate the other of the opposing lateral edges, the at least one pass configured to slidably receive the at least one longitudinal strap and guide the strap through the sheet of material; and
   fastening material attached to the at least one fastener tab and configured to attach to at least one of the at least one strap and the sheet of material so as to secure the sheet of material about the wrist of the wearer,
   wherein portions of the at least one fastener tab and the fastening material overlap one another and remaining portions of the at least one fastener tab and the fastening material are separately attached to opposite surfaces of the free end of the at least one strap.

2. The orthopedic support according to claim 1, further comprising at least one integral strap extending laterally from one of the opposing lateral edges and a distal edge of the sheet of material, and at least one integral strap extending laterally from the other of the opposing lateral edges and a proximal edge of the sheet of material, wherein each integral strap is configured to extend over the opposing lateral edge from which it does not extend.

3. The orthopedic support according to claim 2, wherein each integral strap comprises a fastener tab attached to fastening material that is configured to attach to the sheet of material.

4. The orthopedic support according to claim 1, the longitudinal strap configured to extend over the opposing lateral edge from which it does not extend and circumferentially about the wrist of the wearer.

5. The orthopedic support according to claim 4, wherein the longitudinal strap comprises a fastener tab attached to fastening material that is configured to attach to an outer surface of the longitudinal strap.

6. The orthopedic support according to claim 1, further comprising at least one strap guide secured to an outer surface of the sheet of material, wherein the strap guide is configured to slidably receive the longitudinal strap and guide the strap about the sheet of material.

7. The orthopedic support according to claim 6, further comprising a pair of strap guides injection molded to the outer surface of the sheet of material.

8. The orthopedic support according to claim 1, wherein the at least one pass is injection molded about its outer periphery through a thickness of the sheet of material.

9. The orthopedic support according to claim 1, further comprising at least one strap ring attached to the lateral edge proximate the at least one pass and configured to slidably receive the at least one longitudinal strap therein, wherein the at least one longitudinal strap extending through the strap ring is configured to loop back over itself to tension the strap.

10. The orthopedic support according to claim 1, wherein the at least one fastener tab comprises a polymeric material.

11. The orthopedic support according to claim 1, wherein the at least one fastener tab comprises a prong extending therefrom that is configured to engage the free end of the at least one strap.

12. The orthopedic support according to claim 1, wherein the at least one fastener tab and the sheet of material comprise an outwardly flaring base, and wherein each base is configured to attach to opposite surfaces of the free end of a respective strap.

13. A method for assembling an orthopedic support comprising:
    providing a sheet of material that is flexible and configured to extends around a wrist of a wearer, the sheet of material comprising a pair of opposing lateral edges, at least one integral strap extending laterally from one of the opposing lateral edges and a distal edge of the sheet of material, and at least one integral strap extending laterally from the other of the opposing lateral edges and a proximal edge of the sheet of material, wherein each integral strap is configured to extend over the opposing lateral edge from which it does not extend;
    attaching at least one pass within the sheet of material proximate the other of the opposing lateral edges, the at least one pass configured to slidably receive the at least one longitudinal strap and guide the strap through the sheet of material;
    attaching at least one longitudinal strap to one of the opposing lateral edges of the sheet of material;
    attaching at least one fastener tab to a fastening material such that portions of the fastener tab and the fastening material overlap with one another; and
    attaching remaining portions of the at least one fastener tab and the fastening material to opposite surfaces of a free end of at least one of the integral straps and the longitudinal straps, wherein the attached remaining portions are configured to secure the sheet of material about the wrist of the wearer.

14. The method according to claim 13, wherein attaching the remaining portions of the at least one fastener tab and the fastening material to opposite surfaces of the free end of at least one of the integral straps and the longitudinal straps comprises attaching with at least one of radiofrequency welding, injection molding, and adhering with an adhesive.

15. The method according to claim 13, further comprising attaching at least one strap guide to an outer surface of the sheet of material, wherein the at least one strap guide is configured to slidably receive the longitudinal strap and guide the strap about the sheet of material.

16. The method according to claim 15, wherein attaching the at least one strap guide to the outer surface of the sheet of material comprises injection molding a pair of strap guides to the outer surface of the sheet of material.

17. The method according to claim 13, further comprising attaching at least one pass within the sheet of material, wherein the pass is configured to slidably receive the longitudinal strap and guide the strap through the sheet of material.

18. The method according to claim 17, wherein attaching the at least one pass comprises injection molding the at least one pass about its outer periphery through a thickness of the sheet of material.

19. The method according to claim 13, further comprising attaching at least one strap ring to one of the opposing lateral edges of the sheet of material, wherein the strap ring is configured to slidably receive the at least one longitudinal strap therein.

20. The method according to claim 13, further comprising forming the at least one fastener tab with a polymeric material.

21. The method according to claim 20, wherein forming the at least one fastener tab comprises forming the at least one fastener tab with an injection molding process.

22. The method according to claim 20, wherein forming the at least one fastener tab comprises integrally forming at least one prong with the at least one tab.

23. The method according to claim 22, further comprising engaging the free end of the at least one strap with the at least one prong.

* * * * *

UNITED STATES PATENT AND TRADEMARK OFFICE
CERTIFICATE OF CORRECTION

PATENT NO. : 7,976,487 B2
APPLICATION NO. : 11/609115
DATED : July 12, 2011
INVENTOR(S) : Beth Erin Gramza It is certified that error appears in the above-identified patent and that said Letters Patent is hereby corrected as shown below:

In the Claims:

Column 13
Line 53, in Claim 13, delete "extends" and insert -- extend --, therefor.

Signed and Sealed this
Twenty-third Day of July, 2013

Teresa Stanek Rea
*Acting Director of the United States Patent and Trademark Office*